(12) United States Patent
Kropfeld

(10) Patent No.: US 6,501,826 B1
(45) Date of Patent: Dec. 31, 2002

(54) METHOD FOR THE PRESENTATION OF AN EXAMINATION SUBJECT UPON EMPLOYMENT OF TOMOGRAMS

(75) Inventor: Helmut Kropfeld, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/703,629

(22) Filed: Nov. 2, 2000

(30) Foreign Application Priority Data

Nov. 3, 1999 (DE) .......................... 199 52 942
Oct. 9, 2000 (DE) .......................... 100 49 822

(51) Int. Cl.[7] .......................... H05G 1/64; A61B 6/03; G01N 23/00
(52) U.S. Cl. .......................... 378/98.12; 378/21; 378/4
(58) Field of Search .......................... 378/4, 98.12, 21, 378/62; 382/131; 250/363.04

(56) References Cited

U.S. PATENT DOCUMENTS

| 4,398,213 A | * | 8/1983 | Haendle et al. .......... 378/98.12 |
| 4,926,454 A | * | 5/1990 | Haendle et al. .......... 378/98.12 |
| 5,216,602 A | | 6/1993 | Wolfkiel et al. .......... 378/98.6 |
| 5,307,264 A | * | 4/1994 | Waggener et al. .......... 378/14 |
| 5,377,250 A | | 12/1994 | Hu .......................... 378/15 |
| 5,391,877 A | * | 2/1995 | Marks .................. 250/363.04 |
| 5,871,013 A | * | 2/1999 | Wainer et al. .......... 250/363.04 |

FOREIGN PATENT DOCUMENTS

DE       198 00 946        7/1999

* cited by examiner

Primary Examiner—Drew A. Dunn
(74) Attorney, Agent, or Firm—Schiff Hardin & Waite

(57) ABSTRACT

In a method for the presentation of image information of an examination subject, those tomograms in a series or set of tomograms that differ in terms of the position relative to a dimension are colored, and are subsequently superimposed to form a resultant image. A color having a position on a color scale corresponding to the position of the respective tomogram with respect to the dimension is used to color that tomogram.

31 Claims, 7 Drawing Sheets

```
┌─────────────────────────────────┐
│   GENERATE A SERIES OF          │
│   TOMOGRAMS OF A SUBJECT        │
│   WHICH RESPECTIVELY DIFFER     │
│   IN POSITION WITH REGARD       │
│   TO ONE DIMENSION              │
└─────────────────────────────────┘
                │
                ▼
┌─────────────────────────────────┐
│   COLOR SOME TOMOGRAMS IN       │
│   THE SERIES WITH RESPECTIVE    │
│   COLORS HAVING RESPECTIVE      │
│   POSITIONS ON A COLOR SCALE    │
│   CORRESPONDING TO THE          │
│   RESPECTIVE POSITIONS OF THE   │
│   COLORED TOMOGRAMS WITH        │
│   REGARD TO THE ONE DIMENSION   │
└─────────────────────────────────┘
                │
                ▼
┌─────────────────────────────────┐
│   SUPERIMPOSE AT LEAST          │
│   SOME OF THE COLORED           │
│   TOMOGRAMS TO FORM A           │
│   RESULTANT IMAGE               │
└─────────────────────────────────┘
```

*FIG. 7*

METHOD FOR THE PRESENTATION OF AN EXAMINATION SUBJECT UPON EMPLOYMENT OF TOMOGRAMS

BACKGROUND OF THE INVENTION

1. Field of the Invention The present invention is directed to a method for the presentation of an examination subject by means of tomograms of the type wherein a number of tomograms are produced which differ in position with respect to one dimension such as, for example, each tomogram being allocated to a different time center of gravity or each tomogram being allocated to a different position of a location axis.

2. Description of the Prior Art

Such methods are known, for example, from computed tomography (CT) and serve the purpose of illustrating modifications within the examination subject as a function of time and/or location. A disadvantage of such known methods is that a number of tomograms must be viewed in order to be able to acquire the information with respect to the time or position change.

There is the possibility of presenting the modifications by producing three-dimensional images or with dynamic, cinematic-like presentation of the tomograms; however, the evaluation of such presentations is not always simple since, in particular, the users of CT apparatuses are accustomed to interpreting static, two-dimensional tomograms.

U.S. Pat. No. 5,216,602 discloses showing the blood flow in an examination subject in CT images with the use of an x-ray contrast agent, with the individual pixels of a diagnostically relevant image being compared to the pixels of a reference image, and those pixels of the diagnostically relevant image that deviate in terms of their CT number from the corresponding pixels of the reference image are presented in color, the color corresponding to the extent of the respective deviation.

SUMMARY OF THE INVENTION

An object of the present invention is to provide a method of the type initially described that allows information with respect to a third dimension to be presented in a static tomogram.

This object is inventively achieved by a method for the presentation of an examination subject upon employment of tomograms including the steps of generating a number (series) of tomograms that differ from one another in position with respect to one dimension, coloring some of tomograms in the series of tomograms, with respective colors, whose respective positions on a color scale correspond to the positions of the respective tomograms with respect to the dimension, being allocated to the respective tomograms, and superimposing a number of the color tomograms to form a resultant image.

When three tomograms are colored with the colors red, green and blue, a black-and-white image would arise by superimposition of the colored tomograms if there are no differences whatsoever with respect to the dimension among the tomograms. When, by contrast, differences are present in the three tomograms with respect to the dimension, then an image arises as resultant image that is colored in those regions wherein differences are present with respect to the dimensions, but is a black-and-white image in those regions wherein there are no differences with respect to the dimension.

Thus information with respect to an additional dimension can be presented and recognized in the inventive method in a static tomogram.

The procedure of coloring a tomogram is to be understood as meaning that this operation relates to the tomogram overall, for example by converting all gray-scale values of a black/white image into corresponding red values. In the case of a tomogram that is composed of pixels arranged matrix-like in a manner known from computed tomography, this means that all pixels of the tomogram are affected by the operation of coloring by, for example, the original gray scale value of the respective pixel being replaced by an analogous red value.

In a further version of the invention, the tomograms respectively have substantially the same section plane, and the dimension with respect to which the tomograms differ is the position of the time center of gravity on a time axis, and each tomogram is allocated to a different time center of gravity, and a color is allocated to the respective tomogram to be colored whose position on a color scale corresponds to the position of the time center of gravity of the respective tomogram on the time axis. In this case, all time changes are shown on the basis of color changes.

The term "time center of gravity" means that point in time within the time interval from which the data underlying the tomogram are derived at which half of the data underlying the tomogram are acquired.

Continuous, chronologically successive tomograms, can be produced with the most recently produced tomogram being added at successive points in time to the series of tomograms and inserted, with a tomogram produced earlier from the series of tomograms being removed from the series, and with a number of colored tomograms being superimposed to form a resultant image at each of the following points in time. In this case, the resultant image represents a time window of defined length that is continuously updated. To make the resultant image easily interpretable, the colored tomograms that are superimposed to form a resultant image at each of the successive points include the most recently generated tomogram. Therefore, the point in time (among the aforementioned successive points in time) at which the superimposition takes place occurs after the point in time at which the most recently generated tomogram in the superimposed tomograms was generated.

The resultant images have particular diagnostic effect when the time centers of gravity of successive tomograms superimposed to form a resultant image have identical spacings from one another on the time axis.

The interpretation of a resultant image has a simple form when tomograms are produced that substantially correspond to parallel planes of section.

In a further, preferred embodiment of the invention, the tomograms are of different section planes, with the dimension with respect to which the tomograms differ being the position of the section plane on a location axis, and a color is allocated to the respective tomogram to be colored whose position on a color scale corresponds to the position of the section plane of the respective tomogram on the location axis. In this case, the position of the section planes on the location axis is presented as an additional dimension. This means that those regions that do not coincide in the superimposed tomograms are displayed colored in the resultant image. In contrast thereto, those regions that coincide in the superimposed tomograms are presented in the manner of a black-and-white image.

The term "section plane" means the plane that represents the center plane of the slice of the examination subject scanned in the acquisition of the data underlying the tomogram.

As described above tomograms can be continuously produced, namely for positions following one another along the location axis, with the most recently produced tomogram at successive points in time being added to the series of tomograms and inserted, and the tomogram produced earliest is removed from the series of tomograms, and with the colored tomograms of the series being superimposed to form a resultant image at each of the successive points in time. In this case, the resultant image represents a section on the location axis having a defined length that is continuously updated. As above, for good interpretation of the resultant image a tomogram is used in the superimposition to form a resultant image at each of the successive points in time that is generated for a position along the location axis that lies following the position for which the most recently produced tomogram of the tomograms superimposed to form a resultant image was generated at the preceding point in time.

When the dimension for which the tomograms differ is the position of the section planes on the location axis, in a further embodiment of the invention sets of tomograms are produced in continuous succession for a number of different section planes that respectively have substantially the same time center of gravity as the respective tomograms of a set be colored and superimposed to form a resultant image, whereby a new, resultant image is respectively generated as soon as a new set of tomograms is present. This method is particularly suited for implementation on a CT apparatus having a multi-line detector, whereby each line of the detector can simultaneously generate one tomogram. The slice or slices in which a medical instrument, for example a punction needle, is located in the implementation of an intervention under CT monitoring can then be recognized on the basis of the color in the resultant image.

In order to be able to optimally utilize the information available in the form of tomograms, all tomograms in accordance with the invention are colored in the number of tomograms and all colored tomograms are superimposed.

The tomograms need not be directly produced but, in an embodiment of the invention, can be produced by scanning a volume of the examination subject, and the tomograms are determined from measured data acquired in the scanning, being determined with known methods of multi-planar reconstruction (MPR). This offers the advantage that arbitrary tomograms within the scope of the scanned volume can be utilized for the superimposition.

In a preferred embodiment of the invention, the tomograms are acquired with a CT apparatus, for example a spiral CT apparatus known from German OS 198 00 946, with the location axis corresponding to the system axis of the CT apparatus in the case where the additional dimension is the position of the section planes with respect to a location axis.

The CT apparatus as disclosed by U.S. Pat. No. 5,377,250, can have a detector system with a number of lines of detector elements. In this case in another, preferred embodiment of the invention that the tomograms are acquired with different lines of detector elements, with the positions of the section planes respectively corresponding to the tomograms on the location axis corresponding to the position of the respective line of detector elements with respect to the system axis of the CT apparatus. In this case, the tomograms to be superimposed can be simultaneously generated, i.e. with the same time center of gravity, even though they exhibit differently positioned section planes with respect to the system axis of the CT apparatus.

DESCRIPTION OF THE DRAWINGS

FIG. 7 is a flow chart showing the basic steps of the inventive method.

DESCRIPTION OF THE PREFERRED EMBODIMENTS

Figure 1:
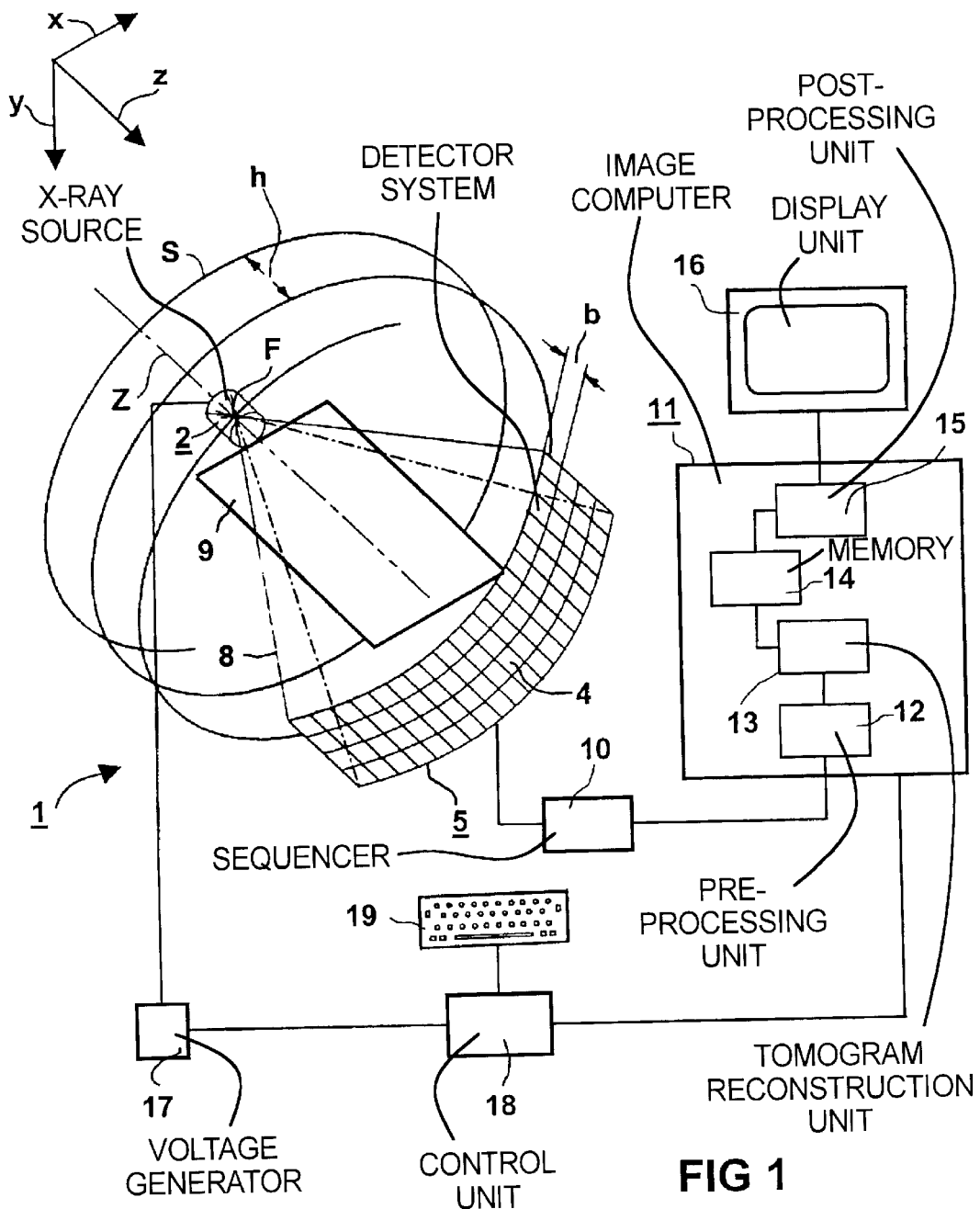
FIG. 1 is a schematic block diagram of a CT apparatus suitable for implementation of the inventive method.
Figure 2:
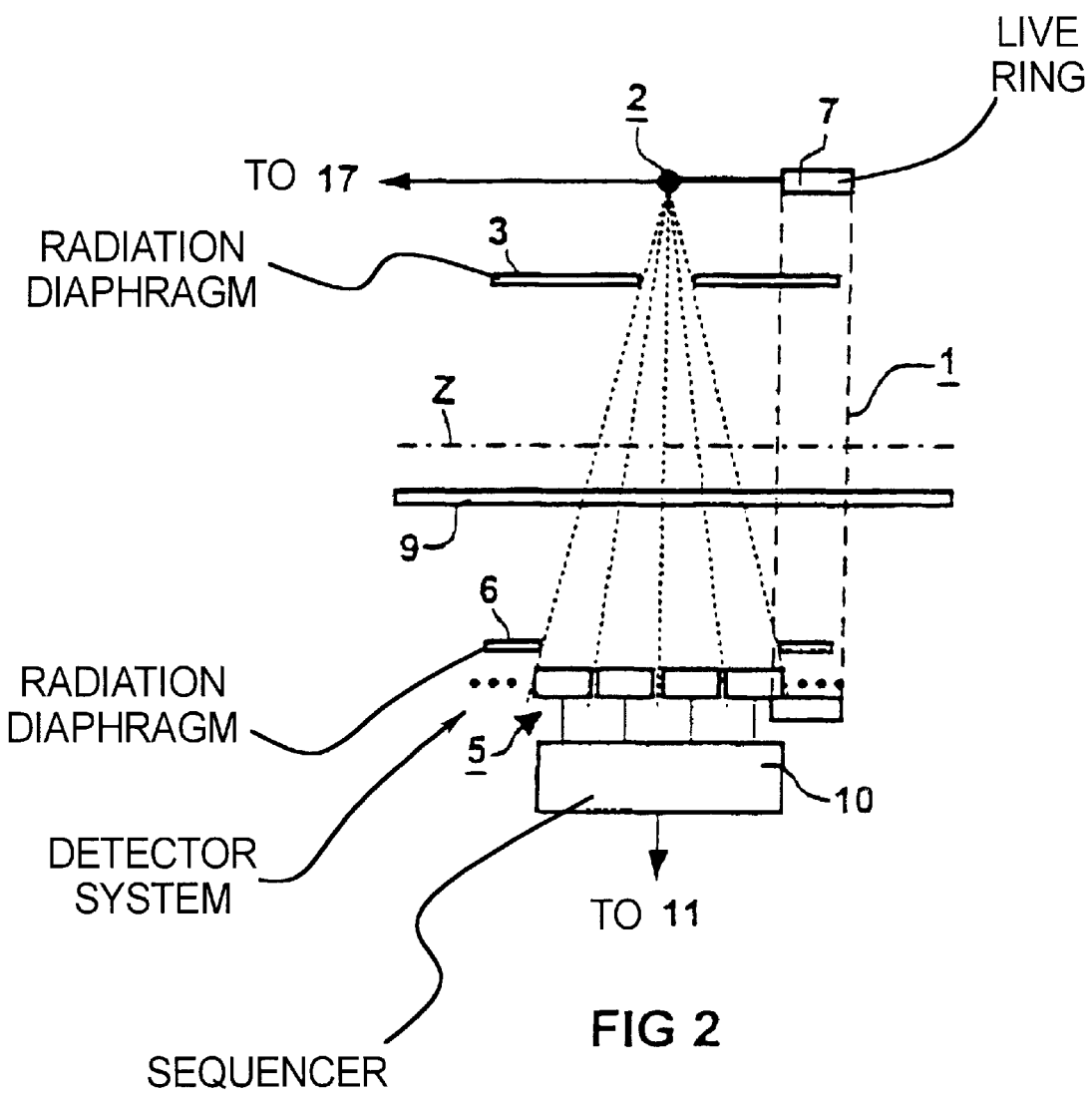
FIG. 2 is a longitudinal section through the apparatus of FIG. 1.

FIGS. 1 and 2 show a CT apparatus of the third generation suitable for implementation of the inventive method. The measuring arrangement 1 thereof includes an x-ray source 2 having a source-proximate radiation diaphragm 3 preceding it (FIG. 2) and a detector system 5 fashioned as a planar array of a number of rows and columns of detector elements—one of these is referenced 4 in FIG. 1—having a detector-proximate radiation diaphragm 6 preceding it (FIG. 2). The x-ray source 2 with the radiation diaphragm 3 and the detector system 5 with the radiation diaphragm 6 are attached to a live ring 7 as shown in FIG. 2 opposite one another. A pyramidal x-ray beam emanating from the x-ray source 2 during operation of the CT apparatus and gated by the adjustable radiation diaphragm 3—the edge rays thereof being referenced 8—is incident on the detector system 5. The radiation diaphragm 6 is thereby set corresponding to the cross-section of the x-ray beam set with the radiation diaphragm 3 so that only that region of the detector system 5 is enabled that can be directly struck by the x-ray beam. These are four rows of detector elements in the operating condition illustrated in FIGS. 1 and 2. Further rows of detector elements covered by the radiation diaphragm 6 are indicated by dots in FIG. 2.

The live ring 7 can be placed into rotation around the system axis Z, by a drive means (not shown). The system axis Z proceeds parallel to the z-axis of a three-dimensional rectangular coordinate system shown in FIG. 1.

The columns of the detector system 5 likewise proceed in the direction of the z-axis transversely relative to the system axis Z, or relative to the z-axis. The rows have a width b measured in the direction of the z-axis which amounts, for example, to 1 mm.

A positioning mechanism 9 that is displaceable parallel to the system axis Z, i.e. in the direction of the z-axis, is provided in order to be able to introduce an examination subject, for example a patient, into the beam path of the x-ray beam.

For implementing an examination of an examination subject, for example a patient, located on the positioning mechanism 9, a scanning of the examination subject ensues with movement of the measuring unit 1 around the system axis Z while a number of projections are registered from different projection directions. The measured data supplied by the detector system 5 thus contain a number of projections.

The measured data read out from the detector elements of each row of the detector system 5 in parallel during the examination of an examination subject are serialized in a sequencer 10 and are transmitted to an image computer 11.

After a pre-processing of the measured data in a pre-processing unit 12 of the image computer 11, the resulting data stream proceeds to a tomogram reconstruction unit 13, which reconstructs tomograms of desired slices of the examination subject from the measured data employing methods with which a person skilled in the art is familiar.

The tomograms reconstructed by the tomogram reconstruction unit 13 are stored in a memory 14 and proceed via a post-processing unit 15 to a display unit 16 connected to the image computer 11, for example a video monitor that displays the tomograms.

The x-ray source 2, for example an x-ray tube, is supplied with the necessary voltages and currents by a generator unit 17. In order to be able to set these to the respectively needed values, the generator unit 17 has a control unit 18 with keyboard 19 allocated to it that allows the necessary settings.

The rest of the operation and control of the CT apparatus also ensues with the control unit 18 and the keyboard 19, which is illustrated in that the control unit 18 is connected to the image computer 11.

In view of the scanning of the examination subject, the CT apparatus allows different operating modes, as follows.

(a) The measuring unit 1, given a stationary positioning device rotates continuously around the system axis Z during an adjustable time duration. From the measured data thereby supplied by a single row of the detector system 5, the tomogram reconstruction unit 13 reconstructs a number of tomograms that are stored in the memory 14 and that do not differ with respect to the position of their section planes on a position axis, namely the axis Z, but do differ in view of a different dimension, namely the position of the time center or gravity of the individual tomograms on a time axis.

(b) Like (a), with the difference that the tomogram reconstruction unit 13 calculates tomograms from the measured data of a number of rows of the detector system 5, these tomograms being stored in the memory 14. The tomograms deriving from different rows of the detector system 5 differ from one another with respect to a dimension, namely the position of their section planes on the system axis Z, in conformity with the spacings of the rows of the detector system measured in the z-direction, since the positions of the section planes of the tomograms on the system axis Z correspond to the positions of the respective rows of the detector system 5 with respect to the system axis Z of the CT apparatus. The tomograms deriving from the same row of the detector system 5 each have the same position on the system axis Z. The tomograms determined for the individual detector rows, however, differ from one another with respect to another dimension, namely in view of the position of their time centers of gravity on a time axis.

(c) The measuring unit 1, given a stationary positioning device 9, is rotated around the system axis Z by an angle that suffices for the complete scanning of the region of the examination subject covered by the measuring unit 1. Subsequently, given a stationary measuring unit 1, the positioning device 9 is shifted in the direction of the system axis Z by a dimension that corresponds to the width of the row of the detector system 5 in the z-direction that is active during the examination, or that corresponds to the width of a number of active rows of the detector system 5 in the z-direction that are active in the examination. Thereafter, the measuring unit I is rotated again by the same angle given a stationary positioning device 9. This is repeated until a desired volume region of the examination subject has been scanned. From the measured data thereby supplied by the detector system 5, the tomogram reconstruction unit 13 calculates a number of tomograms that differ from one another with respect to one dimension, namely the position of their section plane on the system axis Z due to the fact that the corresponding measured data were acquired at different positions of the device 9 relative to the measuring unit 1, and possibly may derive from different rows of the detector system. The tomograms, insofar as the corresponding measured data were acquired given different positions of the positioning mechanism 9 relative to the measuring unit 1, also differ in view of another dimension, namely the position of their time center of gravity on a time axis.

(d) The measuring unit 1 rotates, during an adjustable time duration, continuously around the system axis Z; at the same time, the positioning device 9 is continuously displaced in the direction around the system axis Z relative to the measuring unit 1. A synchronization exists between the rotational movement of the live ring 7 and the translational movement of the positioning device 9 assuring that the ratio of translational to rotational speed is constant. This constant relationship can be set, by selecting a desired value for the feed h of the positioning device per revolution of the live ring 7. The focus F of the x-ray source 2 thus moves—as seen from the examination subject—on a spiral path referenced S in FIG. 1 around the system axis Z. Using the measured data thereby supplied by the detector system 5, the tomogram reconstruction unit 13 calculates planar data sets using known interpolation methods, and tomograms are calculated on the basis thereof and stored in the memory 14 that differ from one another both with respect to a first dimenison, namely the position of their section planes on the system axis Z, and in a second dimension, namely the position of their time centers of gravity on a time axis.

The procedures according to (c) and (d), which are usually referred to as sequence and spiral scanning, respectively are suitable in conjunction with the inventive method for an examination subject or a region of an examination subject that is entirely motion-free, or at least motion-free in the region under examination since, given this pre-condition, the differing position of the tomograms on the time axis can be left out of consideration and the tomograms differ from one another only with respect to one dimension, namely the position of their section planes on the system axis Z.

Whereas, in case of the procedure according to (a), tomograms only can be determined with respect to a single slice defined by the scanning event, since only planar data sets are acquired, this does not apply to the procedures according to (b) through (d). In the procedures according to (b) and (c), different planar data sets are acquired in a direct way, and the procedure (d), different planar data sets are acquired by interpolation, or planar data sets that differ with respect to their position on the system axis Z, are acquired and the image computer 11 combines these to form a volume data set. In the case of the procedures according to (b) through (d), thus, there is the possibility of optionally reconstructing tomograms of the corresponding slices from planar data sets or of reconstructing tomograms from the volume data set having an arbitrary spatial attitude of their section planes using known methods of multi-planar reconstruction (MPR).

Regardless of whether the scanning ensues according to (b), (c) or (d), and regardless of how the tomograms are determined, a number of tomograms that differ from one another with respect to one dimension, namely the position of the corresponding section planes with respect to the system axis Z, are stored in the memory 14 in a first operating mode of the CT apparatus that corresponds to a first embodiment of the inventive method. The post-processing unit 15 colors these images by allocating a color to the respective tomogram whose position on a color scale stored in the image computer 11 corresponds to the position of the section plan of the respective tomogram on the system axis Z. The images colored in this way are superimposed by the post-processing unit 15 to form a resultant image which is displayed on the display unit 16. The basic steps of this procedure are show in FIG. 7.

If all colored and superimposed tomograms were identical, then, dependent on the color scale, a resultant image would arise whose pixels would have a uniform color, and the image information would be contained in the respective brightness of the pixels. The coloring of the tomograms preferably ensues such that a black-and-white image, i.e. a gray scale image, would arise as resultant image for the theoretical case of the presence of identical tomograms.

Since, at least in the case of a biological examination subject, the tomograms generally are not identical in practice, a resultant image arises due to the superimposition that is a black-and-white image in regions wherein the tomograms are identical and that is colored in those regions wherein at least one tomogram differs from the others, so that the resultant image contains information with respect to a further dimension, namely the z-direction, above and beyond the information normally contained in a tomogram.

It is self-evident that an unambiguous interpretation of the resulting image is only possible when the examination subject does not move in the region acquired by the series of tomograms, neither externally nor internally.

Figure 3:
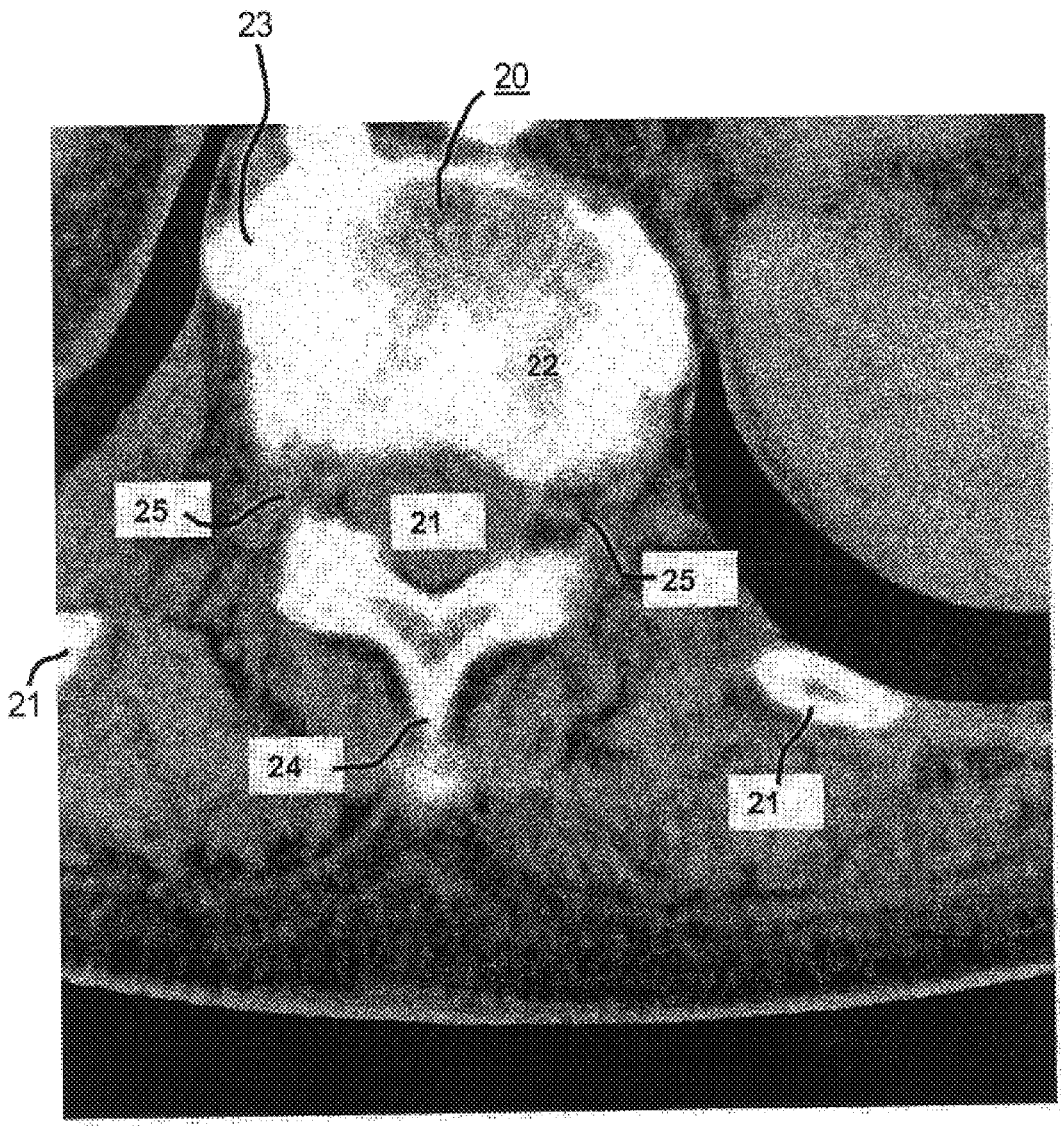
FIGS. 3 through 5 illustrates tomograms to be processed in conformity with the inventive method.
Figure 4:
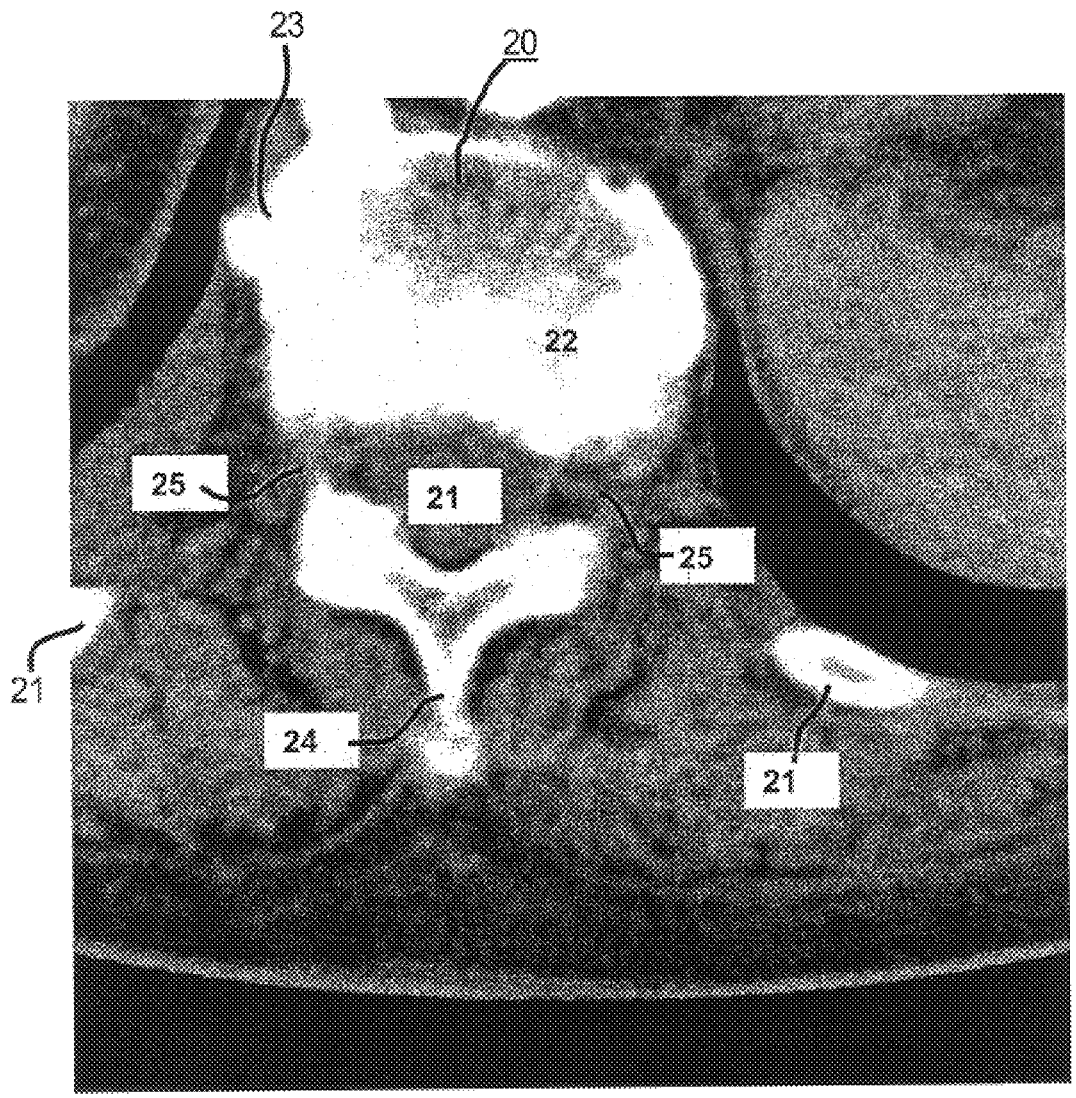
Figure 5:
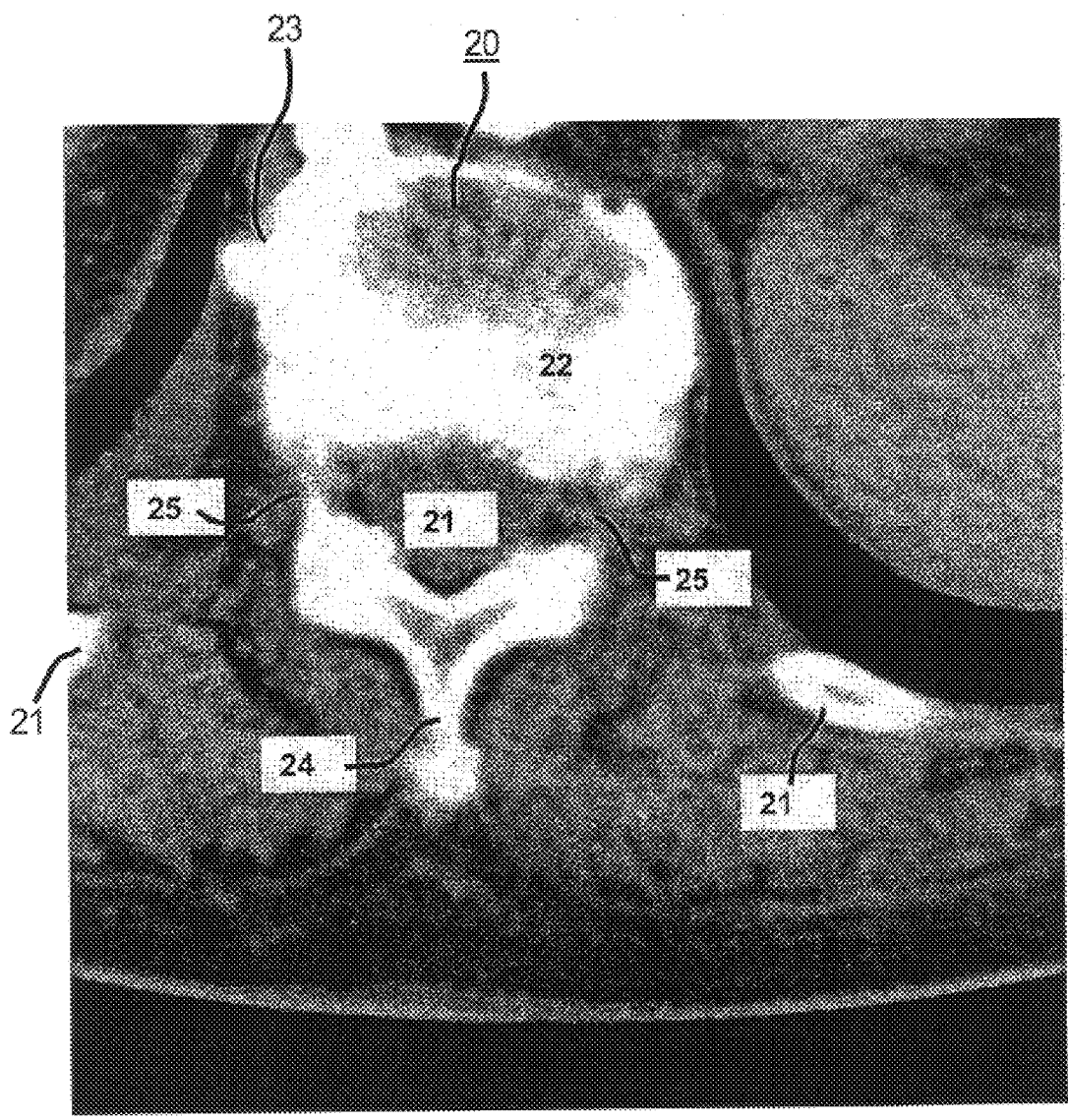

As an example, FIGS. 3 through 5 show three tomograms of a series of tomograms whose section planes exhibit different positions along the system axis Z. FIG. 3 shows the first tomogram, FIG. 4 show a middle tomogram and FIG. 5 shows the last tomogram of the tomograms sorted according to their respective position along the system axis Z. The tomograms that have not yet been colored show the lumbar vertebra 20 of a human examination subject in transversal section before the coloring.

Figure 6:
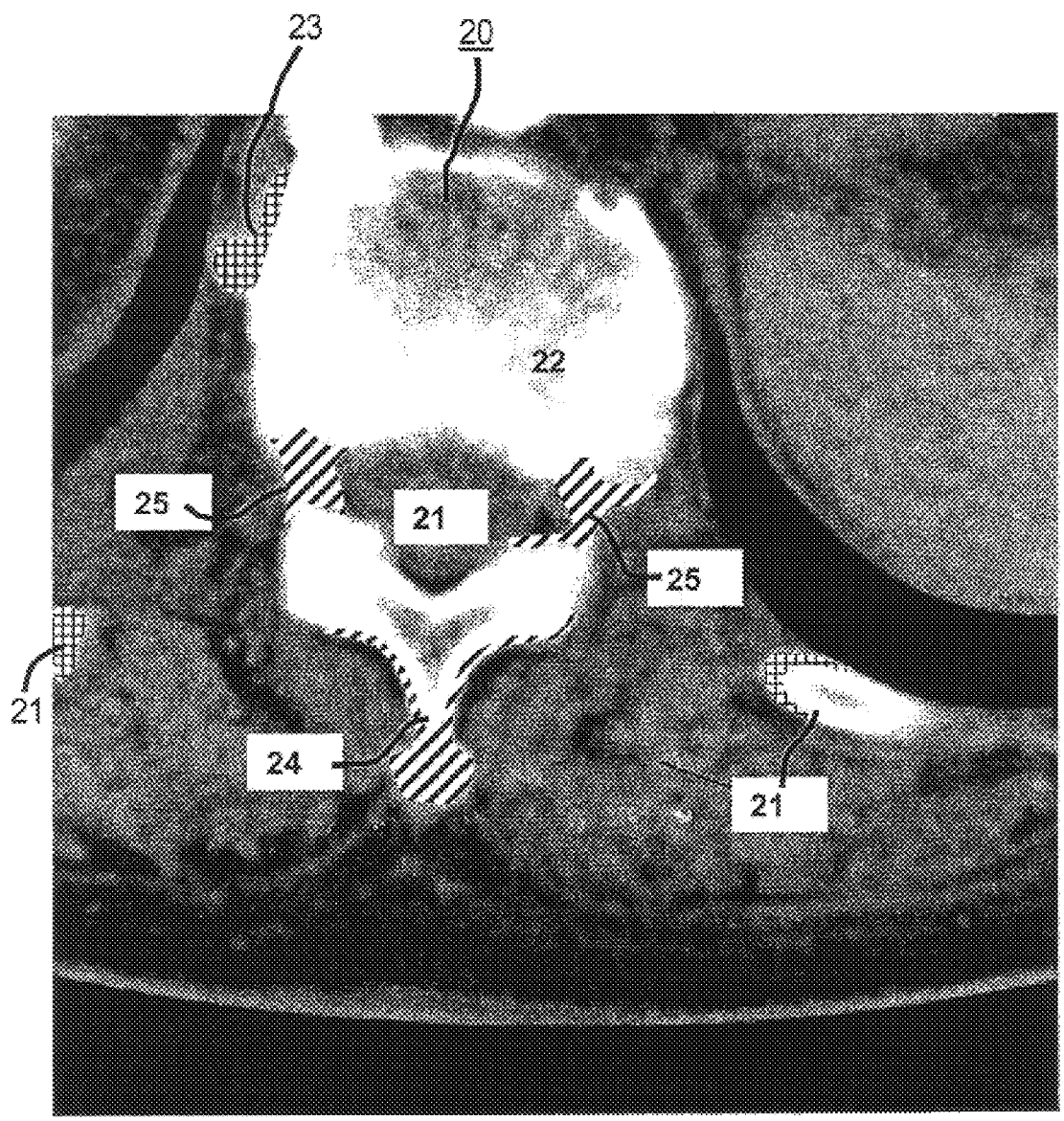
FIG. 6 shows a resultant image generated according to the inventive method by coloring and superimposing the tomograms generated according to FIGS. 3 through 5.

FIG. 6 shows the resultant image. Those regions of the resultant image that would appear highly colored in the color presentation, but which cannot be seen as colored because of the black-and-white illustration of FIG. 6 are identified by a cross-hatching or a diagonal hatching. The cross-hatching thereby corresponds to yellow through red hues and the diagonal hatching corresponds to blue through violet hues.

The color scale is selected such that red through yellow hues correspond to structures which, in terms of center of gravity, are located in regions of the examination subject that are covered by tomograms located at the start of the series of tomograms, and blue through violet hues correspond to structures that lie in regions of the examination subject that appear in tomograms at the end of the series, whereas green hues correspond to structures that are present only in that region of the examination subject that is shown in the middle tomograms of the series.

On the basis of the resultant image, it is clearly apparent that two ribs 21 visible in the resultant image must have a slanting course relative to the section planes of the tomograms, because the ribs 21 in the earlier tomograms of the series appear farther toward the inside than in the later tomograms of the series. It also is clearly apparent that an unspecified structure 23 adjoining the vertebra 22 at the upper left is present, this being more distinctly present in the earlier tomograms of the series than in the later tomograms.

With regard to the blue through violet regions of the resultant image, it is apparent that the vertebral process 24 in the later tomograms of the series is imaged more clearly due to its slanting course relative to the section planes of the tomograms than in the earlier tomograms of the series. Further, the two openings 25 in the vertebra 22 are visible in the resultant image that allow the passage of nerve bundles branching from the spinal cord located in the vertebral canal. As a result of the blue coloring, it is thereby clear that these openings 25 are covered in the early tomograms of the series, whereas the later tomograms of the series already show the edge region of the openings 25.

It thus becomes clear on the basis of the resultant image that, as already explained, the inventive method allows a further dimension to be shown (visualized) in a tomogram, namely the position of structures along the system axis Z in this example.

In an operating mode corresponding to a second embodiment of the inventive method, tomograms that, in a scan of the examination subject according to the procedures (a) or (b), differ from one another with respect to the position of their time centers of gravity on a time axis but agree with respect to the position of their section planes on the system axis Z, are superimposed with the post-processing unit 15 to form a resultant image, and are displayed on the display unit 16. Before the superimposition, the post-processing unit 15 colors the tomograms, with a color whose position on a color scale likewise stored in the image computer 11 corresponds to the position of the time center of gravity of the respective tomogram on the time axis.

As is apparent from the above explanations, structures that move and that are thus imaged at a different position in at least one tomogram of the series of tomograms can be recognized by their chromaticity in the resulting image, whereby, for example, the color scale is selected such that a red through yellow coloring shows the position of their respective structure at the beginning of the time span covered by the plurality of tomograms, a blue through violet coloring shows the position of the structure at the end of the time span covered by the series of tomograms, and a greenish coloring shows the position of the respective structure in the middle region of the time span covered by the series.

Regardless of which of these two embodiments of the inventive method is employed for the operation of the CT apparatus, it is provided in the described exemplary embodiment that, in the memory 14 and at successive points in time, the most recently produced tomogram is added to the series stored in the memory 14 and the tomogram produced earliest is deleted from the series of tomograms stored in the memory 14, for tomograms that are produced continuously chronologically following one another during a time duration that has been set, or that follow one another in their position along the system axis Z, but not all tomograms produced during the time duration are superimposed to form a single, resulting image. The post-processing unit 15 then thus utilizes some tomograms in the tomograms for forming a resultant image that always covers (includes) the most recently produced tomogram, so that the resultant image displayed on the display unit 14 represents the most current available information.

When executing, for example, multi-planar reconstruction with the image computer 11, it is thereby assured that a tomogram at each of the successive points in time, whose time center of gravity lies following the time center of gravity of that tomogram that was newly involved at the respectively preceding point in time in the superimposition to form a resulting image, is newly involved in the superimposition to form a resulting image.

Likewise regardless of the embodiment of the inventive method being used in the momentary operating condition of the CT apparatus, the tomograms in the disclosed exemplary embodiment are continuously generated such that they respectively exhibit identical spacings from one another on the time axis and/or on the location axis.

In a third operating mode of the CT apparatus that corresponds to a third emobidment of the inventive method, the scanning of the examination subject according to (b) ensues such that sets of tomograms are continuously successively produced for a plurality of different planes of section, the tomograms thereof each having substantially the same time center of gravity, i.e. the measured data underlying the tomograms of a set arise from different rows of the detector system 5. The tomograms of a first set are stored in the memory 14 and are colored by the post-processing unit 15, the post-processing unit 15 allocating a color to the respective tomogram whose position on another color scale stored in the image computer 11 corresponds to the position of the plane of section of the respective tomogram on the system axis Z. The images of a set colored in this way are superimposed by the post-processing unit 15 to form a resulting image in which regions in which the tomograms differ from one another appear colored.

For example, the position of a puncture needle in the scanned volume of the examination subject can then be recognized in the resulting image. When the puncture needle is shown in a uniform color, then this means that the puncture needle appears in only a single tomogram, with the color of the needle indicating the position of the needle along the system axis Z, or indicating that tomogram wherein the puncture needle appears. When the puncture needle is shown multi-colored in the resulting image, then the color sequence in which the puncture needle is displayed reveals the respective tomogram in which the puncture needle appears and what angle the puncture needle approximately assumes relative to the location axis.

In order to update the resulting image, for example, in order to be able to continuously monitor the position of the puncture needle, the tomograms of a new set of tomograms are stored in the memory 14 as soon as these tomograms have been produced, and these are colored by the post-processing unit 15 and superimposed to form a new, updated, resulting image that is displayed on the display unit 16 instead of the preceding, resulting image.

Likewise regardless of the embodiment of the inventive method being used, it is provided in the described exemplary embodiment that the tomograms exhibit substantially parallel planes of section; this is assured by the structure of the CT apparatus according to FIGS. 1 and 2 and facilitates the interpretation of the resulting images.

When the method of multi-planar reconstruction is not used in the generation of the tomograms, the structure of the CT apparatus according to FIGS. 1 and 2 likewise provides in the described exemplary embodiment that the planes of section of the tomograms reside substantially at a right angle relative to the location axis, namely the system axis Z.

When the method of multi-planar reconstruction is used, it is provided in the described exemplary embodiment that the tomograms are produced in such a way that their section planes reside substantially at a right angle relative to a location axis that, however, then need not necessarily be identical to the system axis Z but, for example, can proceed at a slant relative thereto.

Regardless of the embodiment of the inventive method with which the CT apparatus operates, an operating mode can be selected wherein all tomograms generated in the image computer 11 are at least temporarily stored in the memory 14 as one tomogram in the series of tomograms;

all tomograms located in the memory 14 are colored by the post-processing unit 15; and all tomograms colored by the post-processing unit 15 are superimposed by this unit to form a resultant image.

Alternatively, operating modes are possible wherein specific tomograms are not utilized for storing in the memory 14 and/or specific tomograms stored in the memory are not colored by the post-processing unit 15 and/or specific, colored images are not taken into consideration by the post-processing unit 15 in the superimposition to form a resultant image.

The structure of the image computer 11 in the exemplary embodiment is described as though the pre-processing unit 12, the tomogram reconstruction unit 13, the memory 14 and the post-processing unit 15 were hardware components. This can in fact be the case, generally, however, certain components are realized by software modules that run on a host computer provided with the required interfaces and that, in a departure from FIG. 1, also can assume the function of the control unit 18 (which is then not needed as a separate unit).

In the exemplary embodiment, the CT apparatus has a detector system 5 with rows whose respective width measured in the z-direction are the same size, for example, 1 mm. Alternatively, a detector system can be provided within the scope of the invention whose rows differ in width. Thus, for example, two inner rows each having a width of 1 mm and respective rows having a width of 2 mm at either side thereof can be provided.

In the exemplary embodiment, the relative movement between the measuring unit 1 and the positioning device 9 is produced by displacing the positioning device 9. However, there is also the possibility within the scope of the invention of leaving the positioning device 9 stationary and instead displacing the measuring unit 1. There is also the possibility within the scope of the invention of generating the necessary relative motion by displacing the measuring unit 1 as well as the positioning device 9.

CT apparatuses of the third generation are employed in conjunction with the above-described exemplary embodiments, i.e. the x-ray source and the detector system are displaced around the system axis in common during the image generation. The invention, however, also can be employed in conjunction with CT apparatuses of the fourth generation wherein only the x-ray source is displaced around the system axis and collaborates with a stationary detector ring, insofar as the detector system is a planar array of detector elements.

The inventive method also can be employed in CT apparatuses of the fifth generation, i.e. CT apparatus wherein the x-radiation emanates not only from one focus but from a number of foci of one or more x-ray sources arrayed around the system axis, insofar as the detector system has a planar array of detector elements.

The CT apparatus employed in conjunction with the above-described exemplary embodiments has a detector system having detector elements arranged in the fashion of an orthogonal matrix. The invention, however, also can be employed in conjunction with a CT apparatus whose detector system has detector elements arranged in some other kind of planar array.

The application of the invention is not limited to computed tomography. The invention is also suitable for employment in conjunction with other tomography methods, for example magnetic resonance tomography, ultrasound tomography, etc.

The above-described exemplary embodiments are directed to the medical application of the inventive method, however, the invention also can be applied beyond medicine, for example in baggage inspection or in examination of materials.

I claim as my invention:

1. A method for presenting image information representing an examination subject, comprising:

generating a series of tomograms which respectively differ in position with regard to one dimension;

coloring some of said tomograms, as colored tomograms, in said series of tomograms with respective colors having respective positions on a color scale corresponding to the respective positions of said colored tomograms with regard to said one dimension; and superimposing at least some of said colored tomograms to form a resultant image.

2. A method as claimed in claim 1 wherein said tomograms in said series each have a section plane, with the respective section planes being substantially the same, and wherein each of said tomograms has a time center of gravity, and wherein said one dimension is a position of the respective time centers of gravities of said tomograms on a time axis, and wherein the step of coloring said tomograms comprises allocating respective colors to said colored tomograms having respective positions on a color scale corresponding to the respective positions of the time centers of gravities of said colored tomograms on said time axis.

3. A method as claimed in claim 2 wherein the step of generating a series of tomograms comprises continuously chronologically generating successive tomograms and, at successive points in time, adding a most recently generated tomogram to said series and deleting an earliest generated tomogram in said series from said series, and wherein the step of coloring at least some of said tomograms includes coloring said most recently generated tomogram, and wherein the step of superimposing said colored tomograms comprises superimposing said colored tomograms at said successive points in time.

4. A method as claimed in claim 3 wherein said most recently generated tomogram is generated at one of said successive points in time and wherein said colored tomograms, including said most recently generated tomogram, are superimposed at another of said successive points in time after said one of said successive points in time.

5. A method as claimed in claim 3 comprising continuously generating said tomograms at substantially identical spacings from each other along a time axis.

6. A method as claimed in claim 3 comprising continuously generating said tomograms at substantially identical spacings from each other along a location axis.

7. A method as claimed in claim 1 comprising generating said series of tomograms in respective section planes that are substantially parallel to each other.

8. A method as claimed in claim 7 comprising generating said tomograms in said section planes disposed substantially at a right angle relative to a location axis.

9. A method as claimed in claim 1 wherein said tomograms have respectively different section planes and wherein said one dimension represents the respective positions of said respective section planes on a location axis, and wherein the step of coloring at least some of said tomograms comprises coloring at least some of said tomograms, as colored tomograms, with respective colors having respective positions on a color scale corresponding to the respective positions of the section planes of the respective tomograms on said location axis.

10. A method as claimed in claim 9 wherein the step of generating a series of tomograms comprises continuously chronologically generating successive tomograms along said location axis and, at successive points in time, adding a most recently generated tomogram to said series and deleting an earliest generated tomogram in said series from said series, and wherein the step of coloring at least some of said tomograms includes coloring said most recently generated tomogram, and wherein the step of superimposing said colored tomograms comprises superimposing said colored tomograms at said successive points in time.

11. A method as claimed in claim 10 comprising superimposing said colored tomograms to form said resultant image at each of said successive points in time including a tomogram produced at a position along said location axis after a position of said most recently generated tomogram.

12. A method as claimed in claim 10 comprising continuously generating said tomograms with substantially identical spacings from each other along said location axis.

13. A method as claimed in claim 12 comprising generating said tomograms in respective section planes that are substantially parallel to each other.

14. A method as claimed in claim 12 comprising generating tomograms with respective section planes disposed substantially at a right angle relative to said location axis.

15. A method as claimed in claim 14 comprising generating said tomograms with substantially equal spacings from each other along a time axis.

16. A method as claimed in claim 9 comprising generating sets of tomograms continuously successively for a plurality of different section planes, each set having a time center of gravity and the respective time centers of gravity of said sets being substantially equal, wherein the step of coloring at least some of said tomograms comprises coloring at least some of said tomograms in each set, and wherein the step of superimposing said color tomograms comprises superimposing the colored tomograms in a set each time a new set of tomograms is generated.

17. A method as claimed in claim 16 comprising continuously generating said sets of tomograms at substantially equal spacings from each other along said location axis.

18. A method as claimed in claim 16 comprising generating said tomograms in said set with respective section planes which are substantially parallel to each other.

19. A method as claimed in claim 17 comprising generating said sets of tomograms with respective section planes disposed substantially at a right angle relative to said location axis.

20. A method as claimed in claim 1 comprising coloring all of said tomograms in said series.

21. A method as claimed in claim 20 comprising superimposing all of said colored tomograms.

22. A method as claimed in claim 1 comprising generating said series of tomograms in a volume of said examination subject by scanning said examination subject to obtain measured data and determining said tomograms from said measured data using a multi-planar reconstruction method.

23. A method as claimed in claim 1 comprising generating said tomograms with a computed tomography apparatus.

24. A method as claimed in claim 23 wherein said computed tomography apparatus has a system axis, and wherein said one dimension is a location axis corresponding to said system axis.

25. A method as claimed in claim 24 comprising generating said tomograms with a computed tomography apparatus having a detector system with a plurality of rows of detector elements, said tomograms being acquired with different rows of said detector elements and wherein each of said tomograms has a section plane along said location axis corresponding to respective positions of said rows of detector elements along said system axis of said computed tomography apparatus.

26. A method as claimed in claim 2 wherein the step of generating a series of tomograms comprises continuously chronologically generating successive tomograms and, at successive points in time, adding a most recently generated tomogram to said series and deleting an earliest generated tomogram in said series from said series, and wherein the step of coloring at least some of said tomograms includes coloring said most recently generated tomogram, and wherein the step of superimposing said colored tomograms comprises superimposing at least some of said colored tomograms at said successive points in time.

27. A method as claimed in claim 26 wherein the step of superimposing said colored tomograms comprises superimposing at least some of said colored tomograms including said most recently generated tomogram.

28. A method as claimed in claim 26 wherein at each of said successive points in time a colored tomogram is included in the step of superimposing said colored tomograms as tomogram generated last with respect to the outer colored tomograms included in the step of superimposing said colored tomograms, and wherein the respective tomogram generated last was generated at a point in time after a point in time at which a tomogram was generated which was included as tomogram generated last in an immediately preceding step of superimposing said colored tomograms.

29. A method as claimed in claim 9 wherein the step of generating a series of tomograms comprises continuously chronologically generating successive tomograms along said location axis and, at successive points in time, adding a most recently generated tomogram to said series and deleting an earliest generated tomogram in said series from said series, and wherein the step of coloring at least some of said tomograms includes coloring said most recently generated tomogram, and wherein the step of superimposing said colored tomograms comprises superimposing at least some said colored tomograms at said successive points in time.

30. A method as claimed in claim 29 wherein the step of superimposing said colored tomograms comprises superimposing at least some of said colored tomograms including said most recently generated tomogram.

31. A method as claimed in claim 29 wherein at each of said successive points in time a colored tomogram is included in the step of superimposing said colored tomograms as tomogram generated last with respect to the positions along said location axis of the other colored tomograms included in the step of superimposing said colored tomograms, and wherein the respective tomogram generated last was generated position along said location axis after a position along said location axis at which a tomogram was generated which was included as tomogram generated last in an immediately preceding step of superimposing said colored tomograms.

\* \* \* \* \*